US007347834B2

(12) United States Patent
Han

(10) Patent No.: US 7,347,834 B2
(45) Date of Patent: Mar. 25, 2008

(54) TRACTION APPARATUS FOR THE CERVICAL VERTEBRAE

(76) Inventor: Jung-Min Han, 409, Grandplaza 802-1, Madu 2-dong, Ilsan-gu, Goyang-city, Gyeonggi-do, 411-352 (KR)

( * ) Notice: Subject to any disclaimer, the term of this patent is extended or adjusted under 35 U.S.C. 154(b) by 303 days.

(21) Appl. No.: 10/555,349

(22) PCT Filed: May 3, 2004

(86) PCT No.: PCT/KR2004/001031

§ 371 (c)(1),
(2), (4) Date: Nov. 1, 2005

(87) PCT Pub. No.: WO2004/098468

PCT Pub. Date: Nov. 18, 2004

(65) Prior Publication Data

US 2007/0055306 A1 Mar. 8, 2007

(30) Foreign Application Priority Data

May 9, 2003 (KR) ........................ 10-2003-0029399

(51) Int. Cl.
*A61F 5/00* (2006.01)
(52) U.S. Cl. ........................................... 602/32; 602/36

(58) Field of Classification Search .................. 602/17, 602/18, 32, 26; 5/622, 636, 637, 640, 644; 128/845, 846, 870
See application file for complete search history.

(56) References Cited

U.S. PATENT DOCUMENTS

| 4,168,459 A | 9/1979 | Roesel, Jr. |
| 4,593,684 A | 6/1986 | Graham |
| 4,736,736 A | 4/1988 | Moers et al. |
| 4,784,122 A | 11/1988 | Graham |
| 5,067,483 A | 11/1991 | Freed |
| 5,569,175 A | 10/1996 | Chitwood |

FOREIGN PATENT DOCUMENTS

KR 10-0367628 12/2002

*Primary Examiner*—Michael A. Brown
(74) *Attorney, Agent, or Firm*—Dickstein Shapiro LLP

(57) ABSTRACT

A traction apparatus for cervical vertebrae for elongating the cervical vertebrae with the cervical vertebrae being stooped in response to the manipulation of a user. Force is only concentrated to the rear part of the neck, such that impact or pressure is not applied to the chin, thereby preventing TMJ disorder and further lengthening the elongation distance of the cervical vertebrae compared with elongating both the chin and rear part of the neck for effectively elongating the cervical vertebrae.

24 Claims, 10 Drawing Sheets

TRACTION APPARATUS FOR THE CERVICAL VERTEBRAE

FIELD OF THE INVENTION

The present invention relates to a traction apparatus for a cervical vertebrae adapted to stretch a patient's cervical vertebrae, thereby allowing him or her to perform a stretching exercise.

BACKGROUND OF THE INVENTION

The vertebral column of a human skeletal frame, often called a spinal column, is formed of a series of bones called the vertebrae. The vertebrae is a flexible column. The head is balanced on top of the column. The skeletal framework of the neck consists of seven cervical vertebrae. The cervical vertebrae has an anatomical structure unlike that of the lumbar vertebrae and thoracic vertebrae, and provides versatile movement for rotation (twisting), flexion and extension.

The cervical vertebrae positioned at the back of the neck region have smaller bones than those of the back and waist, and have a broader moving region than that of the waist. The cervical vertebrae is also exposed to frequent movement, such that they are easily affected by shocks compared with the waist, thus causing frequent pain thereto.

One therapeutic treatment for treating pain caused in the cervical vertebrae is a traction apparatus. Generally, there are four types of traction apparatus for performing the traction of cervical vertebrae.

The first type is a fixed traction apparatus for pushing the neck region to a prescribed level, including the chin, rear part of the neck and shoulder region, via a screw and fixing same. The second type is a power-driven traction apparatus for pulling the chin and rear part of the neck by using a motor while a patient's body is fixed on a bed. The third type is a pneumatic traction apparatus for wrapping the neck region, including the chin and rear part of the neck by an air tube and expanding the air tube in the longitudinal direction of the neck by using a pump to push up and stretch the cervical vertebrae. The fourth type is a traction apparatus for fixing the chin and rear part of the neck and hanging the fixed chin and the rear part of the neck on a horizontal bar to elongate the cervical vertebrae by the patient's weight.

However, there is a serious drawback in the conventional traction apparatus thus described in that a disorder known as Temporomandibular Disorder (TMD), referring to a collection of medical and dental conditions affecting the Temporomandibular Joint (TMJ), may occur because these conventional traction apparatus serve to lift or pull the jaw and back part of the neck at the same time for traction of the cervical vertebrae, and because the cervical vertebrae are positioned at the back of the neck, a strong force can be applied to the jaw when the jaw and the back of the neck are pulled altogether.

For reference, TMJ is a joint located in front of an ear to connect the skull and the maxillary bone, and is connected with muscles related with a mouth opening, closing movements and mastication. TMD can occur when the maxillary bone, TMJ and muscles are not properly positioned and cannot move in harmony, and TMD can easily occur when an excessive shock or pressure is applied to the jaw.

There is another drawback in the conventional traction apparatus of simultaneously pushing or pulling the chin and the back part of the neck in that the elongated distance of the cervical vertebrae is short and an exercise of pulling epiglottis covering the first and second cervical vertebrae cannot be conducted when compared with an apparatus of pulling the rear part of the neck, thereby resulting in an ineffective pulling of the cervical vertebrae.

For example, the first cervical vertebra is a region where the brain connects to the spinal cord through which approximately 30,000 nerve strands pass, and when a structural problem occurs at this region, a disorder occurs at a region governed by the nerve strands and structural deformation can result on the spinal cord and the skull, such that an elongating exercise by way of traction is indispensable.

However, there is a drawback in the conventional traction apparatus of simultaneously pushing or pulling the chin and the back of the neck in that a rear part of the skull is not raised, preventing a proper elongation of the first and second cervical vertebrae, whereas it is necessary to lift the epiglottis of the skull and to elongate the first and second cervical vertebrae in order to evenly transmit the elongation effect to seven cervical vertebrae because the first cervical vertebra is covered by the epiglottis.

SUMMARY OF THE INVENTION

The present invention is disclosed to solve the aforementioned problems and it is an object of the present invention to provide a traction apparatus for cervical vertebrae adapted to concentratively pull only the rear part of the neck close to the cervical vertebrae.

In accordance with a first embodiment of the present invention, the traction apparatus for cervical vertebrae comprises: a first prop for supporting shoulder parts at one side of the first prop; a second prop slidably coupled to the first prop in the longitudinal direction of the cervical vertebrae; moving means for moving the second prop in the longitudinal direction of the cervical vertebrae by way of manipulation of a user; a third prop rotatably coupled at one distal end thereof to the second prop in such a way that the rear part of a head can be laid thereon, the third prop provided with a head support for supporting the border area between the head and neck at one side of the third prop; and lifting means for rotating the third prop in the stooping direction of the neck by way of manipulation of the user.

In accordance with a second embodiment of the present invention, a traction apparatus for cervical vertebrae comprises: a first prop for supporting a shoulder part at one side of the first prop; a second prop slidably coupled to the first prop at one side of the second prop; lifting means for rotating the second prop in the stooping direction of the neck by way of manipulation of the user; a head support formed at the second prop for supporting the border between the neck and the head; and moving means for slidably coupling the head support in the longitudinal direction of the cervical vertebrae and for moving the head support by way of manipulation of a user.

BRIEF DESCRIPTION OF THE DRAWINGS

For a better understanding of the nature and objects of the present invention, reference should be made to the following detailed description with the accompanying drawings, in which.

DETAILED DESCRIPTION OF THE PREFERRED EMBODIMENT

Figure 1:
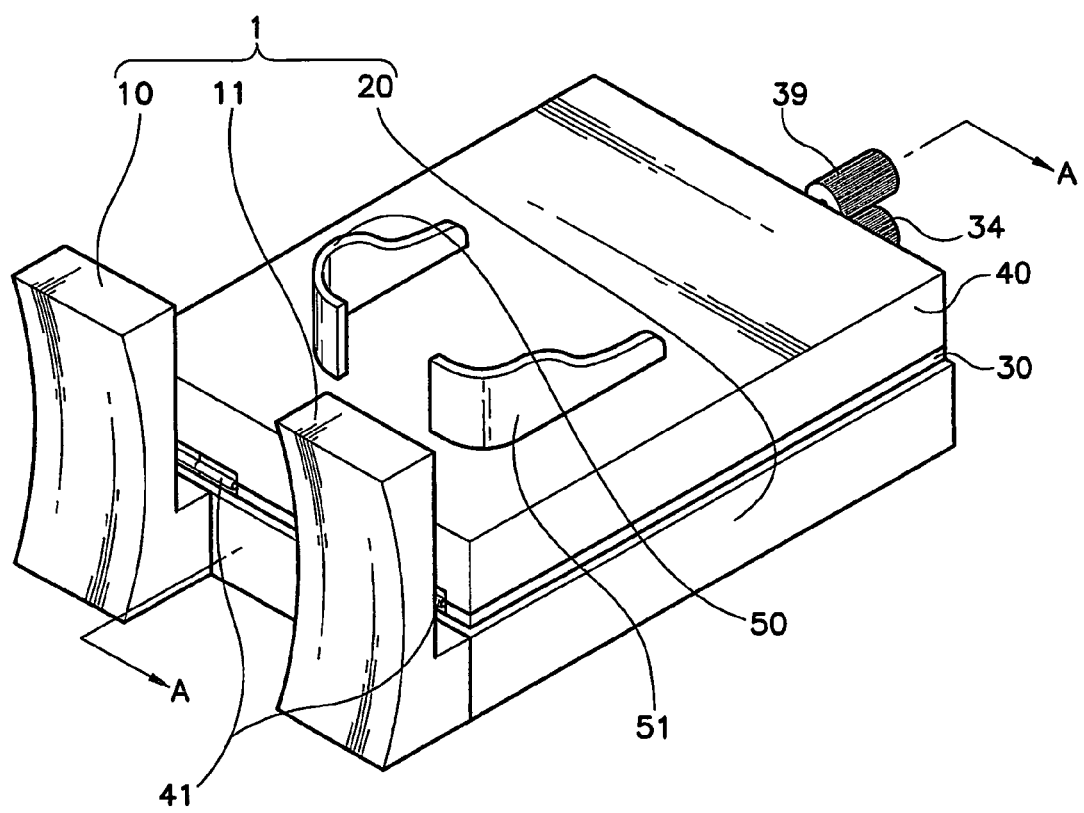
FIG. 1 is a perspective view of a traction apparatus for cervical vertebrae according to the first embodiment of the present invention.
Figure 2:
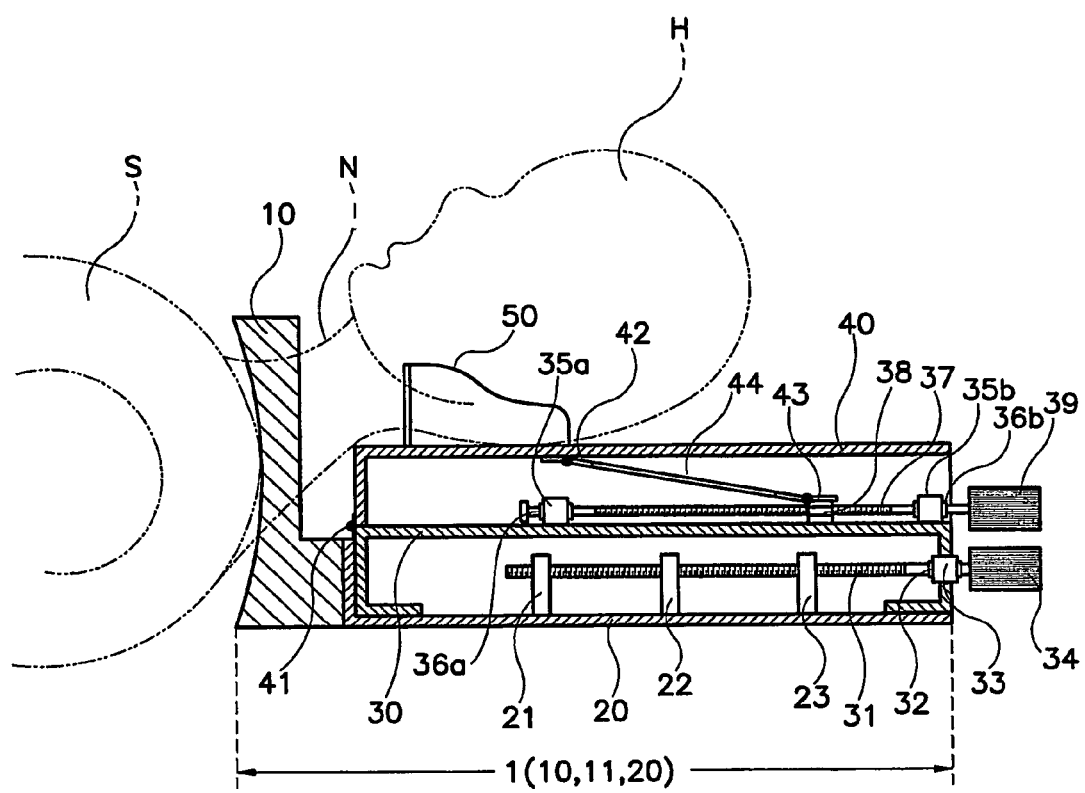
FIG. 2 is a cross-sectional view taken along line AA of FIG. 1.

The preferred embodiments of the present invention will now be described in detail with reference to the annexed drawings. FIG. 1 is a perspective view of a traction apparatus for cervical vertebrae according to the first embodiment of the present invention. FIG. 2 is a cross-sectional view taken along line AA of FIG. 1.

As shown in FIGS. 1 and 2, the traction apparatus for cervical vertebrae according to the first embodiment of the present invention includes a first prop (1), a second prop (30) and third prop (40).

The first prop (1) for supporting shoulder parts at one side of the first prop (1) may be formed as one single member. However, as illustrated in FIGS. 1 and 2, the first prop (1) may be formed with shoulder supports (10,11) at one side of the first prop (1) and a prop (20) at the other side of the first prop (1). The shoulder supports (10,11) and the prop (20) may either be integrally formed or separately formed and coupled together thereafter.

The shoulder supports (10,11) of the first prop (1) are contoured to support to the shoulder parts (S) of a human body, for example, each shoulder part may be concave shaped. The prop (20) at the first support (1) has a shape of a box with a right side thereof being opened, and is fixedly formed at a bottom surface thereof with a plurality of female screw members (21-23) formed with female screw holes in the right and left ends thereof.

The second prop (30) has a shape of an upside down box and is slidably and horizontally coupled to the first prop (1), in other words, in the longitudinal direction of the cervical vertebrae lying on the third prop (40).

Furthermore, the second prop (30) is disposed with a first screw axis (31) circumferentially formed with male threads. The first screw axis (31) passes through a right lateral surface of the second prop (30) to be rotatably fixed by a bearing (32) and a first axis fixation member (33). The first screw axis (31) is then inserted into screw holes of each screw member (21-23) disposed at the prop (20) of the first prop (1). The first screw axis (31) is coupled at a right longitudinal end thereof to a first handle (34) by which a user can easily rotate the first screw axis (31).

The second prop (30) is formed thereon with second and third axis fixation members (35a, 35b) each fixedly disposed at left and right ends thereof and a second screw axis (37) circumferentially formed with male threads and rotatably fixed by the axis fixation members (35a, 35b) and bearings (36a, 36b).

The second screw axis (37) is circumferentially formed with a moving member (38) equipped with female threads corresponding to the male threads and is coupled at a right longitudinal end thereof to a second handle (39) by which a user can easily rotate the second screw axis (37).

The third prop (40) has a shape of an upside down box and is open at the right side thereof. The third prop (40) is disposed on top of the second prop (30) and is rotatably fixed at a left longitudinal end thereof to the second prop (30) via a hinge (41).

Between the third prop (40) and the second prop (30), a connecting member (44) is rotatably fixed at one end thereof to a ceiling of the third prop (40) via a hinge (42) and rotatably fixed at the other end thereof to the moving member (38) via a hinge (43).

The third prop (40) is fixedly formed thereon with head supports (50,51) for supporting a border between the head (H) and the neck (N) in the right direction, i.e., in the direction of the head (H).

Hereinafter, the operational merits of the first embodiment of the present invention thus constructed will be described in detail with reference to the annexed drawings.

First, as illustrated in FIG. 2, the shoulder (S) is arranged to be supported by shoulder supports (10,11) of the first prop (1) and a body is so positioned as to allow the border between the head (H) and the neck (N) to be supported by the head supports (50, 51).

Figure 3:
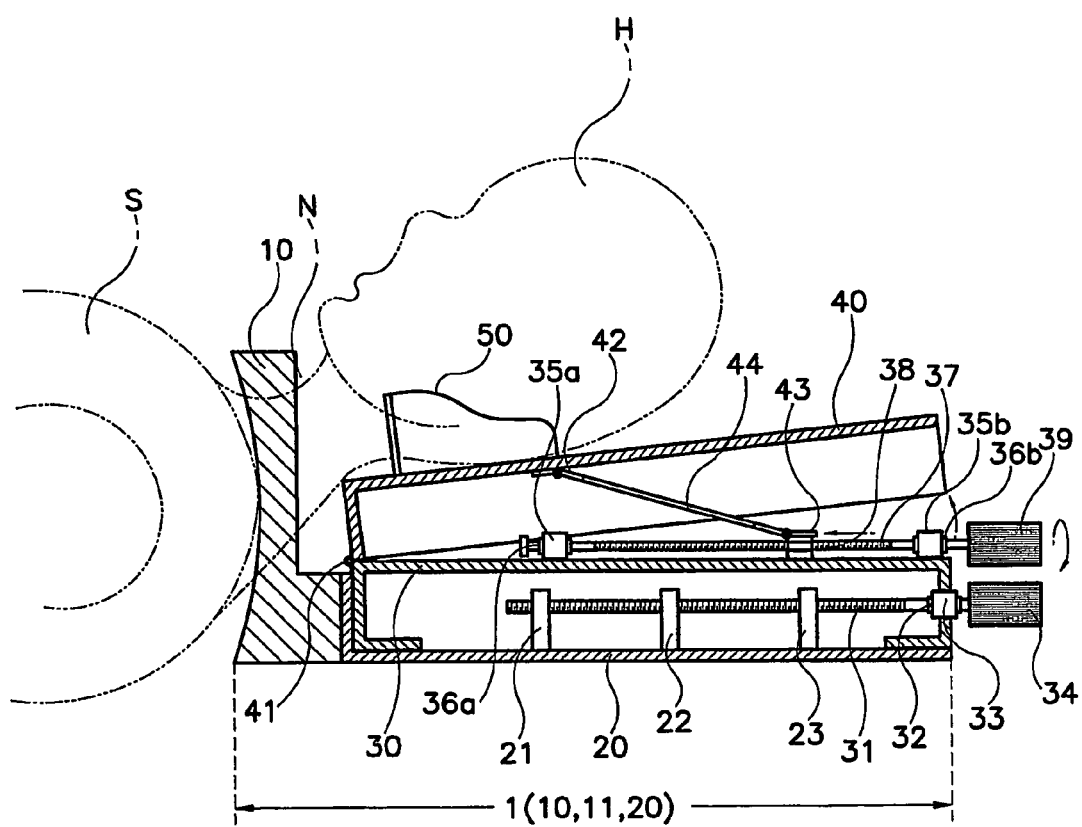
FIG. 3 is a schematic drawing of the third prop of FIG. 2 in a lifted state.

Under these circumstances, as illustrated in FIG. 3, when the second handle (39) is rotated in the clockwise direction in order for a user or a patient to stoop the neck (N) at an appropriate angle, the second screw axis (37) rotates in the clockwise direction to move the moving member (38) to the left in relation with FIG. 3, which inserted into the second screw axis (37).

When the moving member (38) moves to the left (toward the body), the third prop (40) connected to the moving member (38) via a connecting member (44) is rotated about a hinge axle (41) to thereafter be lifted. In other words, the neck (N) of a user can be stooped forward at a desired angle as the third prop (40) is lifted.

Figure 4:
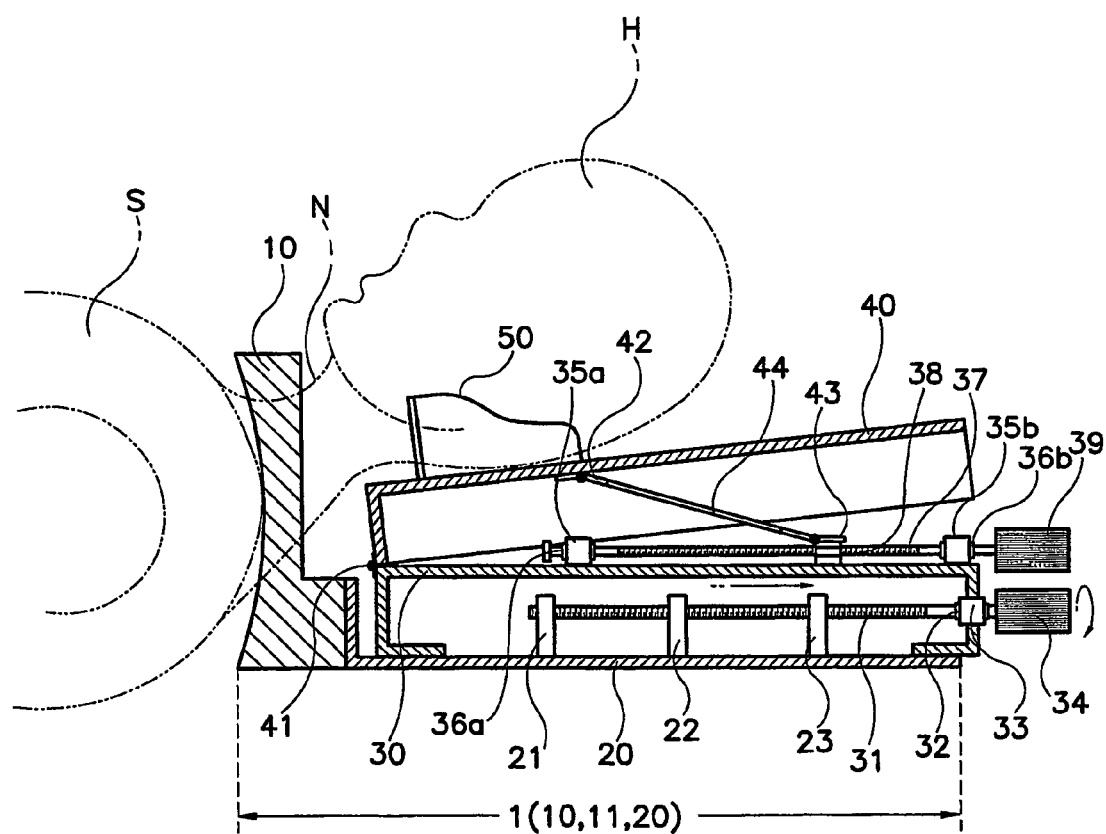
FIG. 4 is a schematic drawing of the second prop of FIG. 3 in an elongated state.

Next, as illustrated in FIG. 4, when the first handle (34) is rotated in the clockwise direction, the first screw axis (31) rotates in the clockwise direction to push each female screw member (21-23) fixed at the prop (20) of the first prop (1) to the left in relation with FIG. 4.

As the first screw axis (31) pushes each female screw member (21-23) of the first prop (1) to the left (toward the body), the second prop (30) consequently moves to the right (away from the body) for elongating the cervical vertebrae of the neck (N). Because the neck (N) of the user is bent forward at a prescribed angle, the neck (N) is elongated at a slight incline from the rear to the front of the neck (N).

In other words, an elongation exercise is carried out with the neck (N) under a slightly stooped state, such that only the rear part of the neck (N) where the cervical vertebrae are located is elongated while the chin is not elongated. As a result, there is no problem of Temporomandibular disorder (TMD), and the elongation distance of the cervical vertebrae is relatively lengthened compared with the back of the neck and the chin being lengthened at the same time, thereby enabling to conduct a concentrated traction of the cervical vertebrae only.

Meanwhile, although the aforementioned operation describes an elongation exercise where the third prop (40) is lifted, the neck (N) is stooped and the second prop (30) is moved, the elongation exercise may be conducted in such a way that the second prop (30) is first moved to lift the third prop (40), or the second and third props (30, 40) are gradually moved and lifted. The third prop 40 is fixedly formed thereon with head supports (50, 51).

Although the first embodiment thus described exemplifies a manually operated construction where a user personally rotates the handles (34, 39), the construction may be embodied in such a way that an actuator (an electric motor, a pneumatic pump, a solenoid or the like) may be applied to a handle part whereby an elongation exercise may be performed by the actuator without direct application on the handle by a user.

Figure 5:
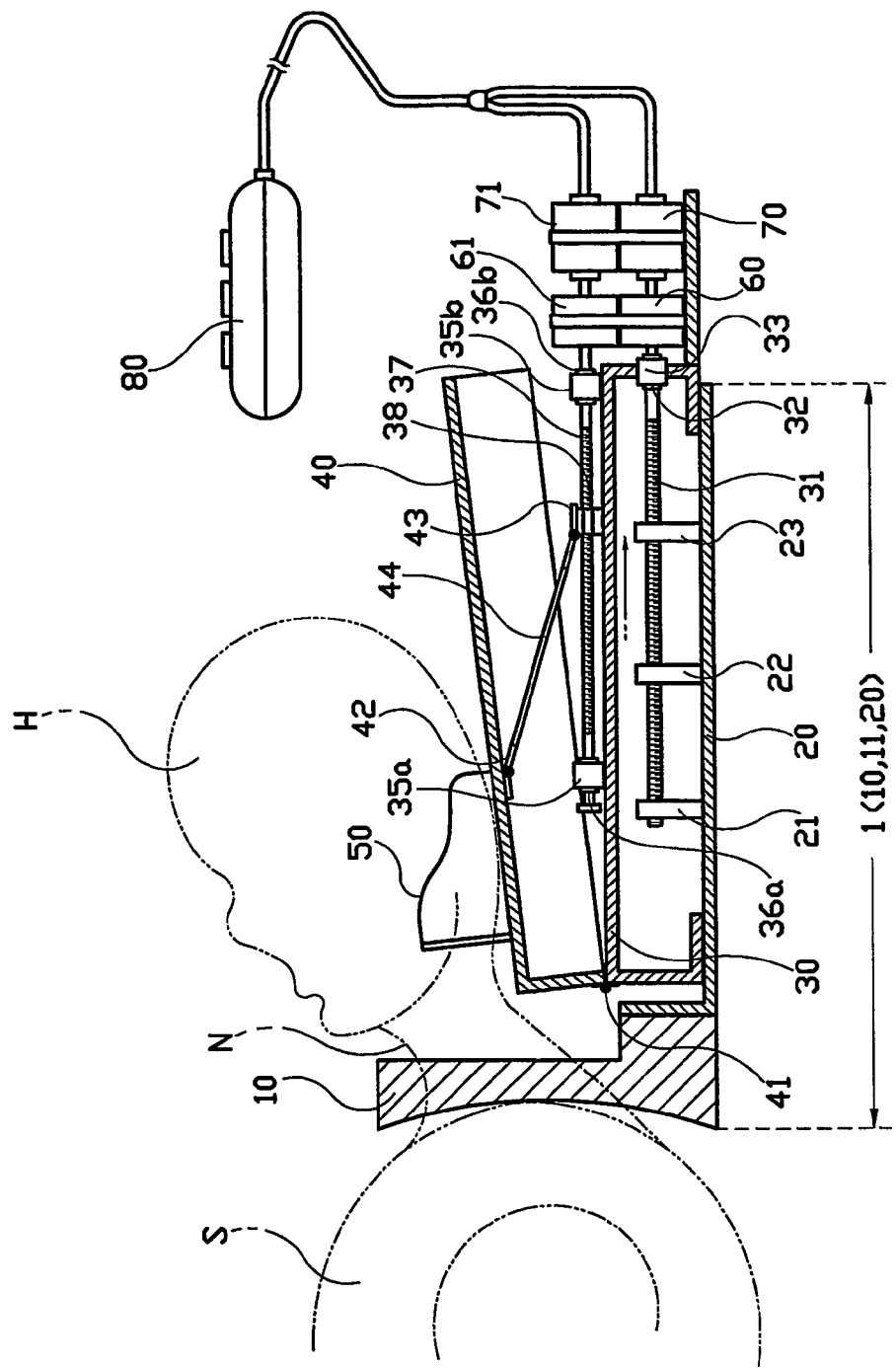
FIG. 5 is a variation of the first embodiment in which an actuator is applied to a handle part instead of a handle.

For example, as illustrated in FIG. 5, preferably, first and second gear boxes (60, 61) are coupled to the first and second screw axes (31, 37) instead of the first and second handles (34, 39), and each gear box (60, 61) is connected to first and second electric motors (70, 71) whereby the first and second electric motors (70, 71) can be driven by the current applied from a manipulation controller (80).

Figure 6:
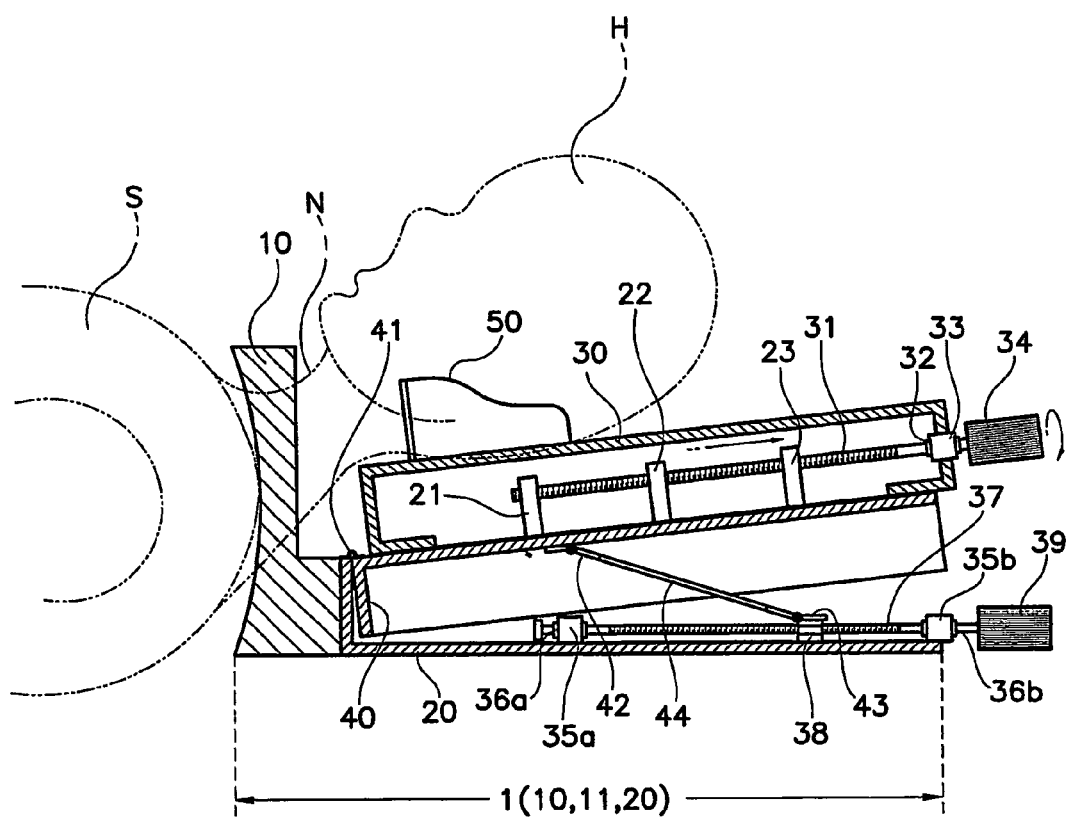
FIG. 6 is a variation of the first embodiment in which the second prop is positioned on the third prop.

As another example, although the first embodiment of the present invention describes a construction where the second prop (30) is arranged underneath the third prop (40), the second prop (30) may be positioned above the third prop (40), as shown in FIG. 6 except that, in this case, the second prop (30) should be rotatably fixed to the first prop (1) via the hinge (41).

Figure 7:
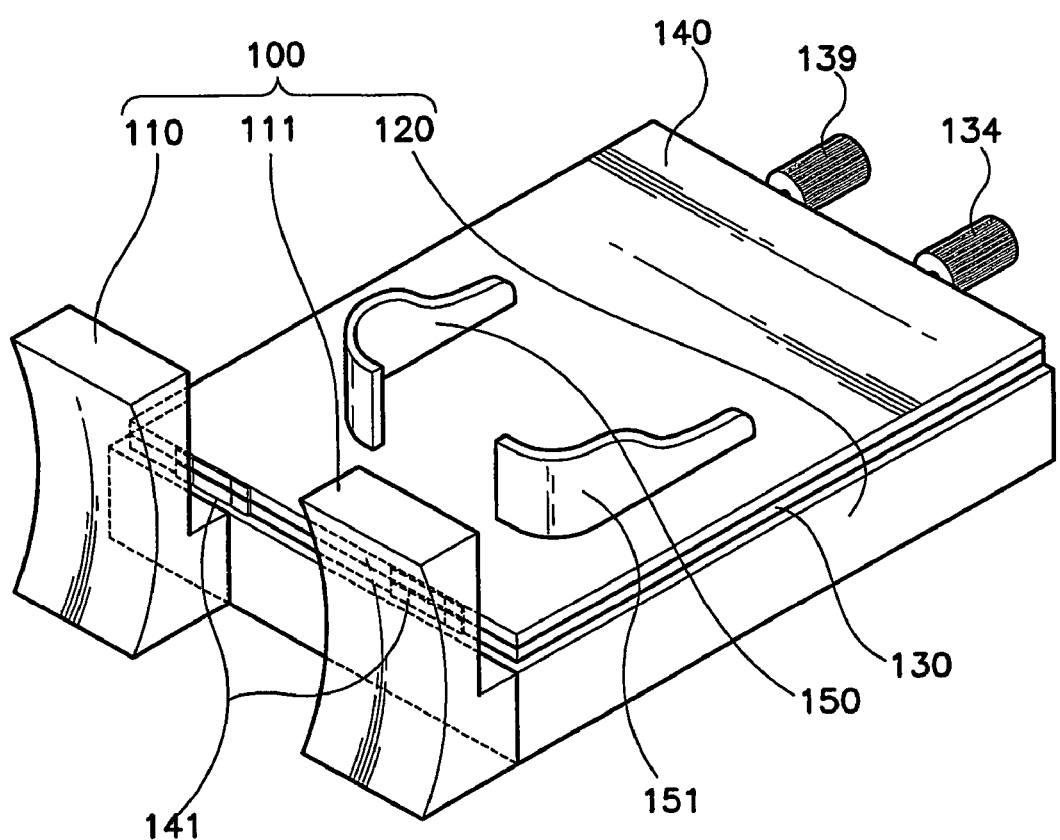
FIG. 7 is a perspective view of a traction apparatus for cervical vertebrae according to the second embodiment of the present invention.
Figure 8:
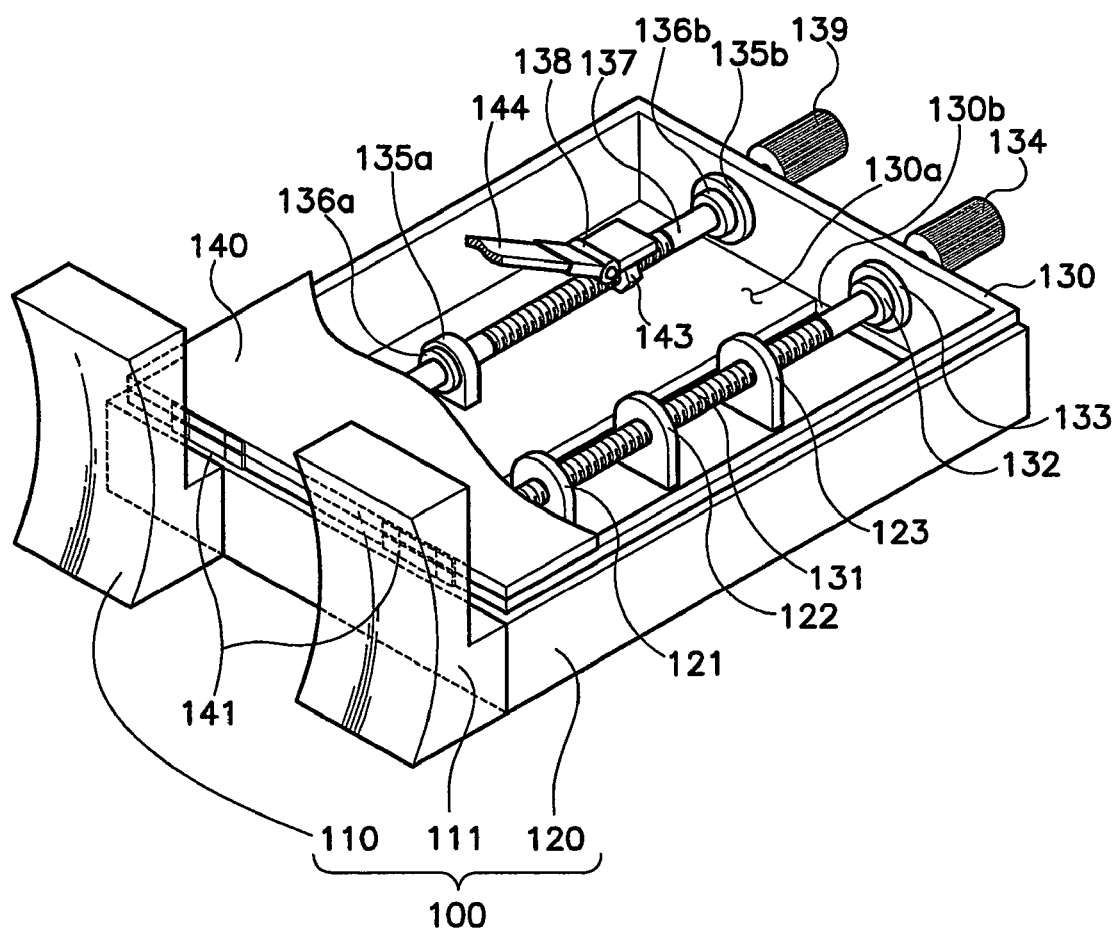
FIG. 8 is a partial cut-out perspective view of FIG. 7.

FIG. 7 is a perspective view of a traction apparatus for cervical vertebrae according to the second embodiment of the present invention and FIG. 8 is a partial cut-out perspective view of FIG. 7. As depicted in FIGS. 7 and 8, a traction apparatus for cervical vertebrae according to the second embodiment of the present invention comprises a first prop (100), a second prop (130) and a third prop (140).

The first prop (100) is designed to support the shoulder part at one side thereof Preferably, the first prop (100) is made of a solid member or constructed with shoulder parts (110,111) at one side and a prop (120) at the other side as shown in FIGS. 7 and 8. Preferably, the shoulder parts (110,111) and the prop (120) are integrally formed, or separately formed and assembled later.

Each shoulder part (110, 111) of the first prop (100) is contoured to support the shoulder part of a body, i.e., concave shape at one side thereof, and the prop (120) of the first prop (100) has a shape of an opened box at the right side, and is fixedly arranged on the floor surface with a plurality of female screw members (121-123) formed with female screw holes, each member spaced out at a prescribed distance.

The second prop (130) of a box shape is horizontally coupled to the first prop (100), i.e., slidably coupled in the longitudinal direction of the cervical vertebrae lying on the third prop (140). A floor surface (130a) of the second prop (130) is opened at one side thereof such that the female screw members (121~123) can be protruded into the second prop (130) when coupled with the first prop (100).

The second prop (130) is disposed with a first screw axis (131) circumferentially formed with male threads. The first screw axis (131) passes through a right lateral surface of the second prop (130) to be rotatably fixed by a bearing (132) and a first axis fixation member (133). The first screw axis (131) is then inserted into screw holes of each screw member (121-123) disposed at the first prop (100). The first screw axis (131) is coupled at a right longitudinal end thereof to a first handle (134) by which a user can easily rotate the first screw axis (131).

Furthermore, the second prop (130) is disposed with a second screw axis (137) circumferentially formed with male threads. The second screw axis (137) passes through a right lateral surface of the second prop (130) to be rotatably fixed by bearings (136a, 136b) and axis fixation members (135a, 135b). The second screw axis (137) is circumferentially inserted by a moving member (138) equipped with female screw holes corresponding to male threads. The second screw axis (137) is coupled at a longitudinal distal end thereof to a second handle (139) by which a user can easily rotate the second screw axis (137).

The third prop (140) of a broad plate shape is arranged on the second prop (130), and is rotatably fixed at a left longitudinal distal end thereof to the second prop (130) via a hinge (141). Between the third prop (140) and the second prop (130), there is disposed a connecting member (144) rotatably fixed at one end thereof to a ceiling of the third prop (140) and rotatably fixed at the other end thereof to the moving member (138) via a hinge (143). The third prop (140) is fixedly formed thereon with head supports (150, 151) for supporting a border between the head (H) and the neck (N) in the right direction, i.e., in the direction of the head (H).

When compared with the first embodiment of the present invention, the second embodiment is different in that the third prop is shaped of a plate and a part where a head of a user is positioned is lowered in height thereof and the overall external appearance looks thin and simple. However, the operational merits and processes between the first and second embodiments are identical.

Meanwhile, although the second embodiment describes that the third prop (140) is lifted in performing the elongation exercise, the head is stooped and the second prop (130) is moved, it should be noted that the second prop (130) may initially be moved to lift the third prop (140), or the second prop (130) and the third prop (140) may be gradually and little by little moved and lifted for conducting the elongation exercise.

In the same context, although the second embodiment thus described exemplifies a manually operated construction where a user personally rotates the handles (134, 139), the construction may be embodied in such a way that an actuator (an electric motor, a pneumatic pump, a solenoid or the like) may be applied to a handle part whereby an elongation exercise may be performed by the actuator without any force from a user being directly applied to the handle.

For example, as illustrated in FIG. 5, preferably, first and second gear boxes are coupled to the first and second screw axes (131, 137) instead of the first and second handles (134, 139), and each gear box is connected to first and second electric motors whereby the exercise may be conducted by the first and second electric motors driven by the current applied from a manipulation controller.

Figure 9:
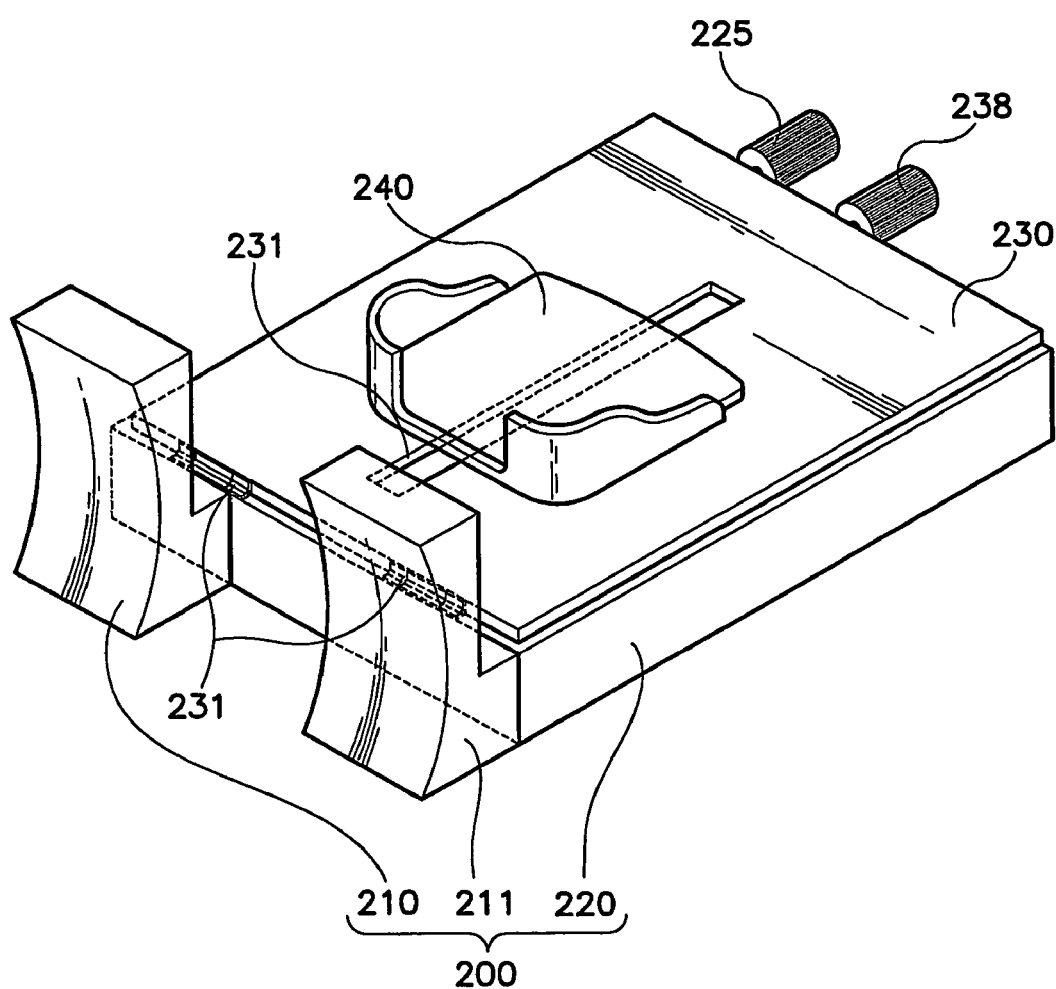
FIG. 9 is a perspective view of a traction apparatus for cervical vertebrae according to a third embodiment of the present invention.
Figure 10:
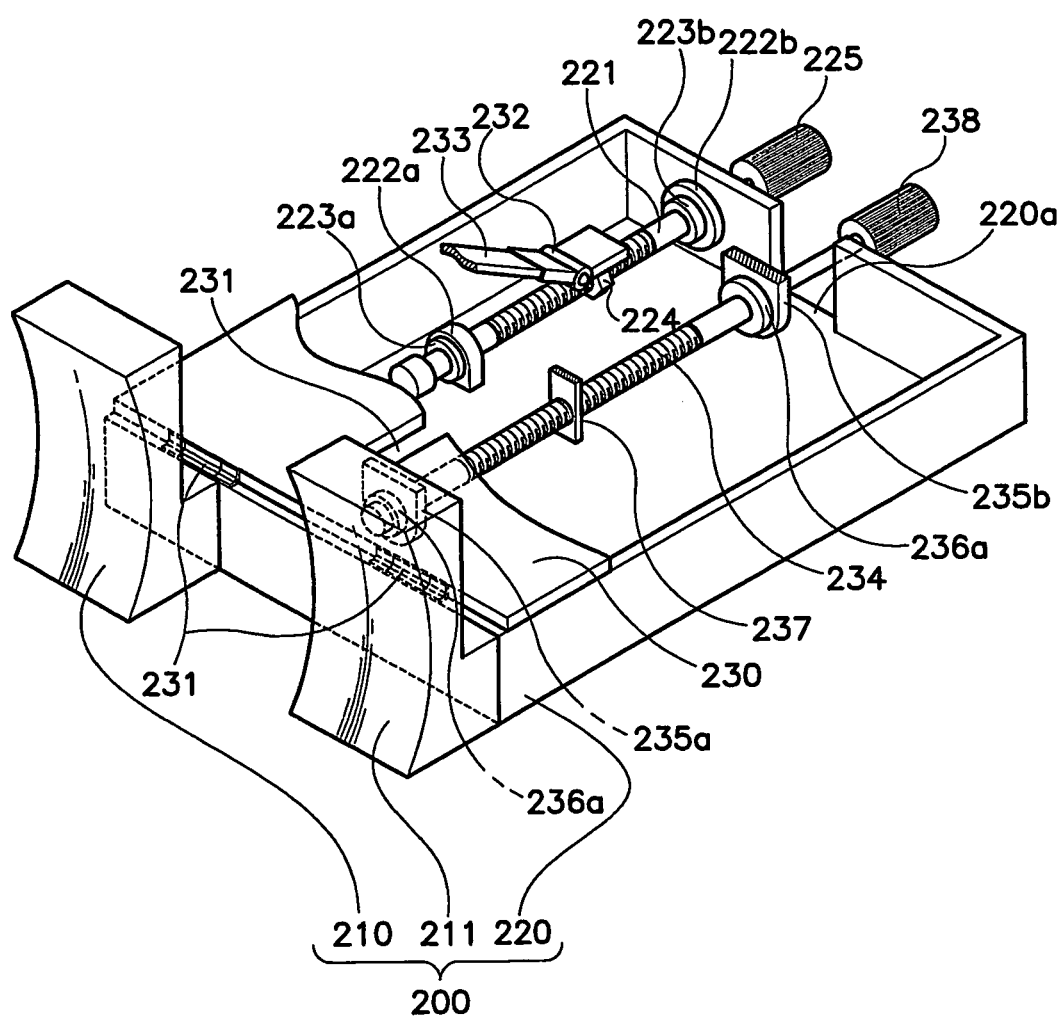
FIG. 10 is a partial cut-out perspective view of FIG. 9.

FIG. 9 is a perspective view of a traction apparatus for cervical vertebrae according to a third embodiment of the present invention and FIG. 10 is a partial cut-out perspective view of FIG. 9. As depicted in FIGS. 9 and 10, a traction apparatus for cervical vertebrae includes a first prop (200), a second prop (230) and a head support (240).

The first prop (200) is designed to support the shoulder part at one side thereof Preferably, the first prop (200) is made of a solid member, or constructed with shoulder parts (210, 211) at one side and a prop (220) at the other side as shown in FIGS. 9 and 10. Preferably, the shoulder parts (210, 211) and the prop (220) are integrally formed, or separately formed and assembled later.

Each shoulder part (210, 211) of the first prop (200) is contoured to support the shoulder part of a body, i.e., concave shape at one side thereof, and the prop (220) of the first prop (200) has a shape of a box with an opening (220a)

at the right side. The prop (220) of the first prop (200) is formed with a first screw axis (221) circumferentially formed with male threads. The first screw axis (221) passes through a right lateral surface of the prop (220) and is rotatably fixed by axis fixation members (222a, 222b) and bearings (223a, 223b).

The first screw axis (221) is circumferentially inserted by a moving member (224) equipped with female threads corresponding to the male threads and is coupled at a right longitudinal distal end thereof with a first handle (225) by which a user can easily rotate the first screw axis (221).

The second prop (230) of a broad plate shape is formed with a guide groove (230a) for guiding the movement of the head support (240) and is arranged on the first prop (200), and is rotatably fixed at a left longitudinal distal end thereof to the first prop (200) via a hinge (231). Between the second prop (230) and the first prop (200), there is disposed a connecting member (233) rotatably fixed at one end thereof to a ceiling of the second prop (230) and rotatably fixed at the other end thereof to the moving member (224) via a hinge (232).

The second prop (230) is formed thereunder with a second screw axis (234) circumferentially formed with male threads. The second screw axis (234) is rotatably fixed via axis fixation members (235a, 235b) each inserted into the prop (220) via an opening (220a) formed at the prop (220) of the first prop (200) and fixed to a ceiling surface of the second prop (230) and bearings (236a, 236b).

The second screw axis (234) is circumferentially inserted by a guide moving member (237) equipped with female thread holes corresponding to the male threads and coupled at one side thereof to a bottom surface of the head support (240) via the guide groove (230a) of the second prop (230). The second screw axis (234) is further coupled at the other longitudinal distal end thereof to a second handle (238) by which a user can easily rotate the second screw axis (234).

The head support (240) supports a border part between the head and the neck in the right direction, i.e., the head direction, and moves along the guide groove (230a) in response to the rotation of the second screw axis (234).

In the third embodiment of the present invention thus described, when the first handle (225) is rotated in the clockwise direction, the first screw axis (221) is rotated in the clockwise direction to lift the second prop (230) and the cervical vertebrae is stooped forward. When the second handle (238) is rotated in the clockwise direction, the second screw axis (234) is rotated in the clockwise direction to move the head support (240) to the right direction (toward the head) and to elongate the cervical vertebrae. The operational merits of the third embodiment are the same as those of the first embodiment. The third embodiment of the present invention is so designed as to reduce the number of parts for simplification of the construction as compared with the first and second embodiments.

Meanwhile, although the third embodiment describes that the second prop (230) is lifted in performing the elongation exercise, the head is stooped and the head support (240) is moved, it should be noted that, in response to a user's desire, the head support (240) may initially be moved to lift the second prop (230), or the second prop (230) and the head support (240) may be gradually and little by little moved and lifted for conducting the elongation exercise.

In the same context, although the third embodiment thus described exemplifies a manually operated construction where a user personally rotates the handles (225, 238), the construction may be embodied in such a way that an actuator (an electric motor, a pneumatic pump, a solenoid or the like) may be applied to a handle part whereby an elongation exercise may be performed by the actuator without any force from a user being directly applied to the handle.

For example, as illustrated in FIG. 5, preferably, first and second gear boxes are coupled to the first and second screw axes (221, 234) instead of the first and second handles (225, 238), and each gear box is connected to first and second electric motors whereby the exercise may be conducted by the first and second electric motors driven by the current applied from a manipulation controller.

As described above, according to the three embodiments of the present invention, the cervical vertebrae are stooped and elongated by which the height of the chine is fixed and only the rear part of the neck is concentratively elongated, thereby enabling to achieve an effective traction of the cervical vertebrae. A further detailed explanation of the traction of the cervical vertebrae is provided below.

The cervical vertebrae are lopsidedly aligned from the middle to the back section of a neck, and when the back of the neck is concentratively depressed, resistance of unflexible tissues can be reduced. Blood vessels, gullet and respiratory tract that are positioned at the front of cervical vertebrae can be protected.

Furthermore, considering that most of the disorders in a cervical vertebral region occur in the rear part of the cervical vertebrae, it is preferable that the back of the neck should be concentratively elongated. For example, in case of prolapsus of intervertebral disks, the back of the cervical vertebrae should be elongated as in the present embodiments such that the curvature of the cervical vertebrae can be straightened and the intervertebral foramen positioned at the back of the cervical vertebrae can be lifted to effectively reduce pressure to nerve roots because the cervical vertebrae have a shape of "C" opening to the rear of the neck.

Furthermore, in order to transmit the elongation effect to the entire seven cervical vertebrae, the larynx of the skull should be lifted to elongate the number one and two cervical vertebra. However, the method of pulling or pushing both the chin and the rear part of the neck according to the prior arts cannot lift the larynx of the skull and properly elongate the number one and two vertebra, whilst according to the present invention, the cervical vertebrae can be stooped slightly in the forward direction and elongated such that the traction exercise can be conducted with the larynx of the skull covering the number one and two cervical vertebra being lifted, thereby enabling to evenly transmit the elongation effect to the seven cervical vertebrae.

The foregoing description of the preferred embodiments of the present invention has been presented for the purpose of illustration and description. It is not intended to be exhaustive or to limit the invention to the precise form disclosed, and modifications and variations are possible in light of the above teachings or may be acquired from practice of the invention. It is intended that the scope of the invention be defined by the claims appended hereto, and their equivalents.

As apparent from the foregoing, there is an advantage in the traction apparatus for cervical vertebrae thus described according to the embodiments of the present invention in that force is not applied to the chin but is only concentrated to the rear part of the neck such that impact or pressure is not applied to the chin, thereby preventing TMJ disorder and further lengthening the elongation distance of the cervical vertebrae compared with elongation of both the chin and the rear part of the neck, and effectively elongating the cervical vertebrae because the larynx of the skull covering the number one and two cervical vertebra is lifted.

There is another advantage in that cervical vertebrae lopsidedly positioned toward the back of the neck are concentratively depressed by which resistance of unflexible tissues that protect and encompass blood vessels, gullet and respiratory tract that are positioned at the front of cervical vertebrae can be reduced, and more effective and safer elongation exercises can be conducted.

There is still another advantage in that the inclined angle of the neck can be adjusted to a safe and comfortable position at any time before or after the elongation or in the midst of the elongation for a patient who has a deformation in the overall structure of the cervical vertebrae, and a patient can adjust the position of the neck and the intensity of the elongation force by himself or by herself.

What is claimed is:

1. A traction apparatus for cervical vertebrae comprising:
   a first prop for supporting shoulder parts at one side of said first prop;
   a second prop slidably coupled to said first prop in the longitudinal direction of the cervical vertebrae;
   moving means for moving said second prop in the longitudinal direction of the cervical vertebrae by way of manipulation of a user;
   a third prop rotatably coupled at one distal end thereof to said second prop in such a way that a rear part of a head can be laid thereon, said third prop provided with a head support for supporting a border area between the head and neck at one side of said third prop; and
   lifting means for rotating said third prop in the stooping direction of the neck by way of manipulation of the user.

2. The apparatus as defined in claim 1, wherein said moving means comprises:
   a screw axis formed with male threads and rotatably fixed to any one side of said first and second prop;
   a female screw member formed with female threads correspondingly to be screwed to said male threads of said screw axis and rotatably fixed to any remaining other side of said first and second prop; and
   a rotating member equipped at one distal end of said screw axis for rotating said screw axis in response to the manipulation of a user.

3. The apparatus as defined in claim 1, wherein said lifting means comprises:
   a screw axis formed with male threads and rotatably fixed at any one side of said second and third prop;
   a moving member formed with female threads correspondingly to be screwed to said male threads of said screw axis;
   a connecting member rotatably fixed at one side thereof to said moving member and rotatably fixed at the other side thereof to any remaining side of said second and third prop; and
   a rotating member equipped at one distal end of said screw axis for rotating said screw axis in response to the manipulation of a user.

4. A traction apparatus for cervical vertebrae comprising:
   a first prop for supporting a shoulder part at one side of said first prop;
   a second prop where a rear part of a head can be laid, and equipped at one side of said second prop with a head support for supporting a border between the head and the neck;
   a third prop rotatably coupled at one distal end thereof to said first prop and slidably coupled thereon to said second prop in the longitudinal direction of the cervical vertebrae;
   moving means for moving said second prop in the longitudinal direction of the cervical vertebrae in response to the manipulation of a user; and
   lifting means for rotating said third prop in the stooping direction of the neck in response to the manipulation of a user.

5. The apparatus as defined in claim 4, wherein said moving means comprises:
   a screw axis formed with male threads and rotatably fixed to any one side of said second and third prop;
   a female screw member formed with female threads correspondingly to be screwed to said male threads of said screw axis and rotatably fixed to any remaining other side of said second and third prop; and
   a rotating member equipped at one distal end of said screw axis for rotating said screw axis in response to the manipulation of a user.

6. The apparatus as defined in claim 4, wherein said lifting means comprises:
   a screw axis formed with male threads and rotatably fixed at any one side of said first and third prop;
   a moving member formed with female threads correspondingly to be screwed to said male threads of the screw axis;
   a connecting member rotatably fixed at one side thereof to said moving member and rotatably fixed at the other side thereof to any remaining side of said first and third prop; and
   a rotating member equipped at one distal end of said screw axis for rotating said screw axis in response to the manipulation of a user.

7. A traction apparatus for cervical vertebrae comprising:
   a first prop for supporting a shoulder part at one side of said first prop;
   a second prop rotatably coupled at one distal end thereof to said first prop;
   lifting means for rotating said second prop in the stooping direction of a neck in response to the manipulation of a user;
   a head support equipped at said second prop for supporting a border between a head and the neck; and
   moving means for slidably coupling said head support in the longitudinal direction of the cervical vertebrae and for moving said head support in response to the manipulation of a user.

8. The apparatus as defined in claim 7, wherein said lifting means comprises:
   a screw axis formed with male threads and rotatably fixed at any one side of said first and second prop;
   a moving member formed with female threads correspondingly to be screwed to said male threads of said screw axis;
   a connecting member rotatably fixed at one side thereof to said moving member and rotatably fixed at the other side thereof to any remaining side of said first and second prop; and
   a rotating member equipped at one distal end of said screw axis for rotating said screw axis in response to the manipulation of a user.

9. The apparatus as defined in claim 7, wherein said moving means comprises:
   a screw axis formed with male threads and rotatably fixed to said second prop;
   a female screw member formed with female threads correspondingly to be screwed to said male threads of said screw axis and fixed to said head support; and a rotating member equipped at one distal end of said screw axis for rotating said screw axis in response to the manipulation of a user.

10. The apparatus as defined in claim 1, wherein said first prop comprises a shoulder support for supporting a shoulder part at one side of said first prop and a prop at the other side of said first prop.

11. The apparatus as defined in claim 2, wherein said rotating member is a handle to be held and rotated by a user.

12. The apparatus as defined in claim 2, wherein said rotating member comprises:
   an actuator for receiving a current to generate a rotational force; and
   a manipulation controller for applying an operating current to the actuator in response to the manipulation of a user.

13. The apparatus as defined in claim 4, wherein said first prop comprises a shoulder support for supporting a shoulder part at one side of said first prop and a prop at the other side of said first prop.

14. The apparatus as defined in claim 7, wherein said first prop comprises a shoulder support for supporting a shoulder part at one side of said first prop and a prop at the other side of said first prop.

15. The apparatus as defined in claim 3, wherein said rotating member is a handle to be held and rotated by a user.

16. The apparatus as defined in claim 5, wherein said rotating member is a handle to be held and rotated by a user.

17. The apparatus as defined in claim 6, wherein said rotating member is a handle to be held and rotated by a user.

18. The apparatus as defined in claim 8, wherein said rotating member is a handle to be held and rotated by a user.

19. The apparatus as defined in claim 9, wherein said rotating member is a handle to be held and rotated by a user.

20. The apparatus as defined in claim 3, wherein said rotating member comprises:
   an actuator for receiving a current to generate a rotational force; and
   a manipulation controller for applying an operating current to the actuator in response to the manipulation of a user.

21. The apparatus as defined in claim 5, wherein said rotating member comprises:
   an actuator for receiving a current to generate a rotational force; and
   a manipulation controller for applying an operating current to the actuator in response to the manipulation of a user.

22. The apparatus as defined in claim 6, wherein said rotating member comprises:
   an actuator for receiving a current to generate a rotational force; and
   a manipulation controller for applying an operating current to the actuator in response to the manipulation of a user.

23. The apparatus as defined in claim 8, wherein said rotating member comprises:
   an actuator for receiving a current to generate a rotational force; and
   a manipulation controller for applying an operating current to the actuator in response to the manipulation of a user.

24. The apparatus as defined in claim 9, wherein said rotating member comprises:
   an actuator for receiving a current to generate a rotational force; and
   a manipulation controller for applying an operating current to the actuator in response to the manipulation of a user.

* * * * *